United States Patent
Charles

(10) Patent No.: US 11,806,105 B2
(45) Date of Patent: Nov. 7, 2023

(54) VITREORETINAL SURGERY DEXTERITY ENHANCEMENT SYSTEM

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 360 days.

(21) Appl. No.: 17/151,829

(22) Filed: Jan. 19, 2021

(65) Prior Publication Data

US 2021/0220067 A1 Jul. 22, 2021

Related U.S. Application Data

(60) Provisional application No. 62/963,728, filed on Jan. 21, 2020.

(51) Int. Cl.
*A61B 34/00* (2016.01)
*A61B 34/37* (2016.01)

(52) U.S. Cl.
CPC .............. *A61B 34/72* (2016.02); *A61B 34/37* (2016.02); *A61B 34/75* (2016.02)

(58) Field of Classification Search
CPC .......... A61B 34/37; A61B 34/72; A61B 34/75
See application file for complete search history.

(56) References Cited

U.S. PATENT DOCUMENTS

| | | | |
|---|---|---|---|
| 5,710,870 A | 1/1998 | Ohm et al. | |
| 5,784,542 A | 7/1998 | Ohm et al. | |
| 5,943,914 A | 8/1999 | Morimoto et al. | |
| 6,000,297 A | 12/1999 | Morimoto et al. | |
| 6,016,607 A | 1/2000 | Morimoto et al. | |
| 6,330,837 B1 | 12/2001 | Charles et al. | |
| 6,516,681 B1 * | 2/2003 | Pierrot ................. | B25J 17/0266 901/23 |
| 6,702,805 B1 | 3/2004 | Stuart | |
| 6,723,106 B1 | 4/2004 | Charles et al. | |
| 7,892,243 B2 | 2/2011 | Stuart | |

(Continued)

FOREIGN PATENT DOCUMENTS

RU 2491161 C1 8/2013

OTHER PUBLICATIONS http://www.preceyes.nl/preceyes-surgical-system/, accessed Oct. 24, 2019 (8 pages).

*Primary Examiner* — Ashley L Fishback
(74) *Attorney, Agent, or Firm* — PATTERSON + SHERIDAN, LLP

(57) ABSTRACT

The present disclosure relates to high dexterity manipulation systems for microsurgical procedures. The surgical system includes a master apparatus controllably coupled to a slave apparatus configured to couple to a patient's head with a dual tripod structure having two pluralities of linear actuator links pivotally supporting a surgical tool shaft. The motions of the linear actuator links are controlled to provide at least 6 degrees of freedom for the surgical tool shaft. The slave apparatus may further include a redundant axis rotatable tool shaft, thus enabling 7 degrees of freedom for a surgical tool. The surgical system includes sensors enabling forces of interaction between the slave apparatus and its environment to be reflected back to the master apparatus. Forces imparted onto the master apparatus by an operator can be fed forward to control the slave apparatus and scaled down to reduce the forces on target tissues.

18 Claims, 10 Drawing Sheets

(56) References Cited

U.S. PATENT DOCUMENTS

| | | |
|---|---|---|
| 9,480,532 B2 | 11/2016 | Stuart |
| 9,549,781 B2 | 1/2017 | He et al. |
| 9,554,865 B2 | 1/2017 | Olds et al. |
| 9,662,174 B2 | 5/2017 | Taylor et al. |
| 9,770,828 B2 | 9/2017 | Taylor et al. |
| 9,854,969 B2 | 1/2018 | Smith et al. |
| 9,877,648 B2 | 1/2018 | Farley et al. |
| 10,172,686 B2 | 1/2019 | Charles |
| 10,188,552 B2 | 1/2019 | He et al. |
| 10,376,328 B2 | 8/2019 | Charles et al. |
| 10,406,026 B2 | 9/2019 | Simaan et al. |
| 10,413,374 B2 | 9/2019 | Chassot et al. |
| 10,561,470 B2 | 2/2020 | Hourtash et al. |
| 10,617,561 B2 | 4/2020 | Meenink |
| 10,646,990 B2 * | 5/2020 | Olds ................. B25J 9/0051 |
| 10,856,943 B2 | 12/2020 | Stefanchik et al. |
| 10,898,281 B2 | 1/2021 | Cooper et al. |
| 10,905,509 B2 | 2/2021 | Naus et al. |
| 10,917,543 B2 | 2/2021 | Ramirez Luna et al. |
| 2003/0005786 A1 | 1/2003 | Stuart et al. |
| 2010/0275718 A1 | 11/2010 | Stuart et al. |
| 2010/0331858 A1 * | 12/2010 | Simaan ................. A61B 34/30 |
| | | 623/1.11 |
| 2018/0353252 A1 | 12/2018 | Chassot et al. |
| 2019/0223967 A1 | 7/2019 | Abbott et al. |

* cited by examiner

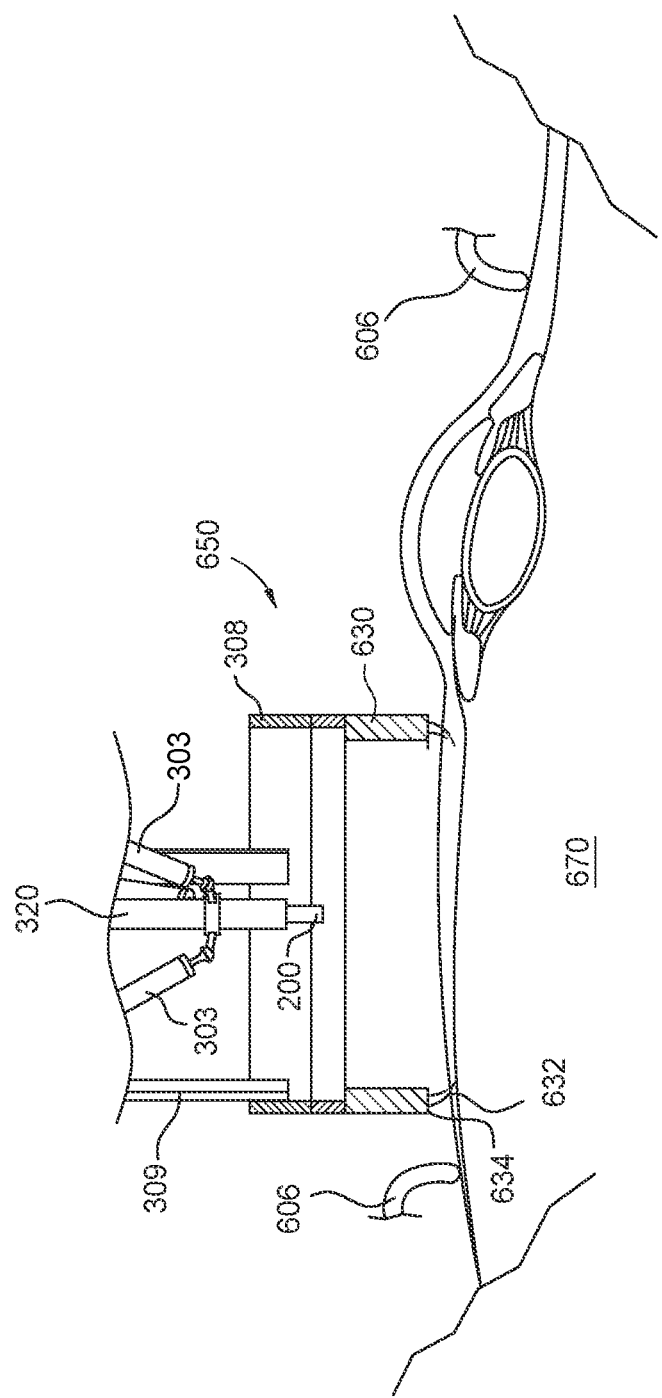

VITREORETINAL SURGERY DEXTERITY ENHANCEMENT SYSTEM

PRIORITY CLAIM

This application claims the benefit of priority of U.S. Provisional Patent Application Ser. No. 62/963,728 titled "VITREORETINAL SURGERY DEXTERITY ENHANCEMENT SYSTEM," filed on Jan. 21, 2020, whose inventor is Steven T. Charles, which is hereby incorporated by reference in its entirety as though fully and completely set forth herein.

BACKGROUND

Field

Embodiments of the present disclosure generally relate to manipulation systems for surgical procedures, and more particularly, high dexterity manipulation systems for ophthalmic microsurgical procedures.

Description of the Related Art

Retinal microsurgery, and in particular, vitreoretinal surgery, is among one of the most challenging groups of procedures in the field of ophthalmologic surgical practice. As the name implies, vitreoretinal eye surgery is performed in the gel-like vitreous and on surfaces of the light-sensitive retina within the relatively small ocular space. Common conditions necessitating vitreoretinal surgery (e.g., vitrectomy) include epimacular membranes, vitreomacular schisis, vitreomacular traction syndrome, diabetic traction retinal detachments, proliferative vitreoretinopathy (PVR), retinal detachment, macular holes, as well as various microinjection procedures for gene and cell based therapies.

During vitreoretinal surgery, surgeons must perform precise micron-scale maneuvers while applying diminutive forces to retinal tissues beyond the natural human levels of sensory perception. Thus, performance of vitreoretinal surgery is inherently restricted by human sensory and motor limitations, surgeon fatigue and hand tremor, imprecise instrumentation, fine feature sizes, limited operating room within the ocular space, and occasionally poor visualization of the interior of the eye. In addition to the above limitations, serious complications may also be caused by involuntary patient eye and/or head movement. The aforementioned factors may contribute to a variety of complications including retinal breaks, retinal detachment, hemorrhage, damage to retinal blood vessels, and damage to the lens resulting in cataracts, many of which can develop into potentially irreversible damage and visual impairment.

Recently, robotically assisted surgical devices have been developed to assist surgeons in the performance of minimally invasive ophthalmic surgeries, including vitreoretinal surgery. Despite the advantages of robotic surgery, traditional ophthalmic surgical techniques may be preferred for these types of procedures. While this is partly due to high equipment costs, the absence of effective mechanisms to deal with patient movement and the sensory and motor limitations of surgeons have been accepted as crucial technical disadvantages. To minimize the risk of complications from patient eye movement, some current robotic ophthalmic surgical systems utilize digital eye tracking. However, tracking technology is limited in current robotic designs and is not advanced enough to detect and correct for sudden head and eye movements, which may be caused by sleep apnea or a startled response upon awakening from sedation. Furthermore, most current robotic ophthalmic surgical systems do not provide force control (e.g., scaling, limiting, filtering) or force feedback (e.g., tactile feedback) while maintaining a high degree of freedom of movement, and instead typically only provide some form of scaling.

Additional limitations associated with robotically assisted surgical devices are that currently proposed robotic systems only have 4 degrees-of-freedom (4-DOF) and rely on robots having serial kinematics. 4-DOF is insufficient to address patient head and/or eye movement or rotate the eye to visualize around corneal or lens opacities, as well as visualize the peripheral retina during ophthalmic procedures. Further, serial robots such as articulated robotic arms are disadvantaged by cumulative joint error, kinematic singularities, decreased precision, and longer cycle times resulting in decreased speed. Thus, current robotically assisted surgical devices lack the dexterity to precisely and effectively execute the micron-scale maneuvers regularly performed during vitreoretinal surgery and respond to sudden head and eye movement of the patient.

Accordingly, what is needed in the art are improved methods and apparatus for improving the dexterity and accuracy of ophthalmic microsurgical procedures.

SUMMARY

The present disclosure generally relates to manipulation systems for surgical procedures, and more particularly, high dexterity manipulation systems for ophthalmic microsurgical procedures.

In one embodiment, a surgical system is provided. The surgical system includes a master apparatus and a slave apparatus controllably coupled to the master apparatus and further configured to be mounted to a patient's head. The slave apparatus includes a support frame having a base and three or more support columns extending from the base in a first orientation. A first and second set of three hydraulically-driven and linear-actuating links are coupled to the support columns by spherical joints at proximal ends thereof. The slave apparatus further includes a surgical tool pivotally supported by each of the links directly or indirectly coupled thereto at distal and proximal ends of the surgical tool and configured to provide translational and rotational movement to the surgical tool. The surgical system also includes a hydraulically driven rotary actuator to provide rotational movement to the surgical tool coupled to the first and second sets of links.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 6C illustrates a perspective view of an example slave apparatus mounted to a patient's head, according to certain embodiments of the present disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to manipulation systems for surgical procedures, and more particularly, high dexterity manipulation systems for ophthalmic microsurgical procedures. In one embodiment, a surgical system includes a master apparatus controllably coupled to a slave apparatus. The slave apparatus is configured to couple to the head of a patient and includes a dual tripod structure having two pluralities of linear actuator links pivotally supporting a surgical tool shaft. The motions of the linear actuator links is controlled by saline hydraulics to provide at least 6 degrees of freedom for the surgical tool shaft during use thereof. In one embodiment, the slave apparatus further includes a redundant axis rotatable tool shaft, thus enabling 7 degrees of freedom for a surgical tool coupled thereto. The surgical system includes a plurality of sensors enabling forces of interaction between the slave apparatus and its environment to be reflected back to the master apparatus to provide a sense of force sensed by a tool or end effector coupled to the slave apparatus. Forces imparted onto the master apparatus by an operator can be fed forward to control the slave apparatus and scaled down to reduce the forces on target tissues. Accordingly, the surgical system enhances the dexterity of an operator and enables the operator to perform medical procedures more easily than by hand.

Figure 1:
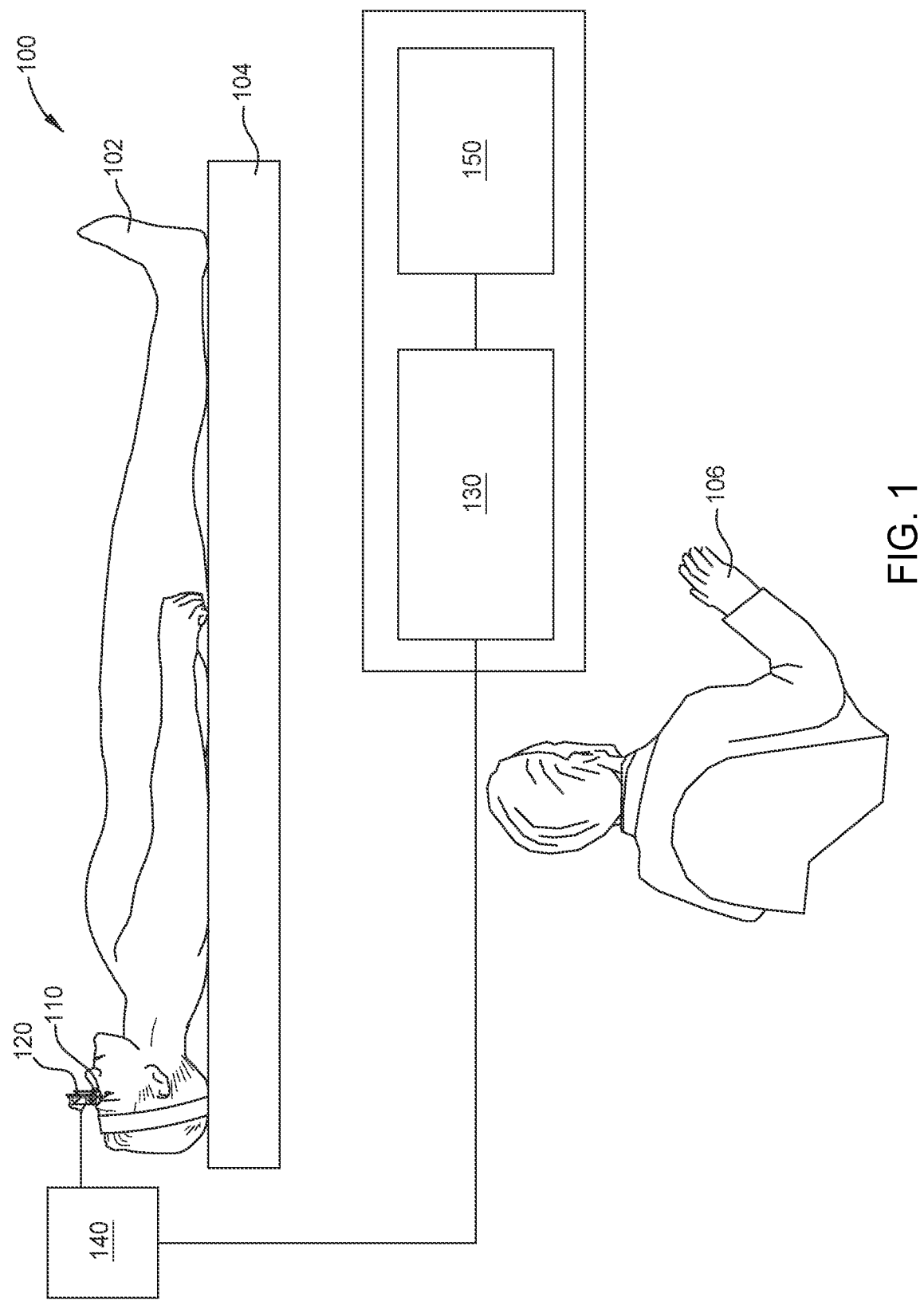
FIG. 1 illustrates a schematic view of an exemplary surgical manipulation system, according to certain embodiments of the present disclosure.
Figure 2:
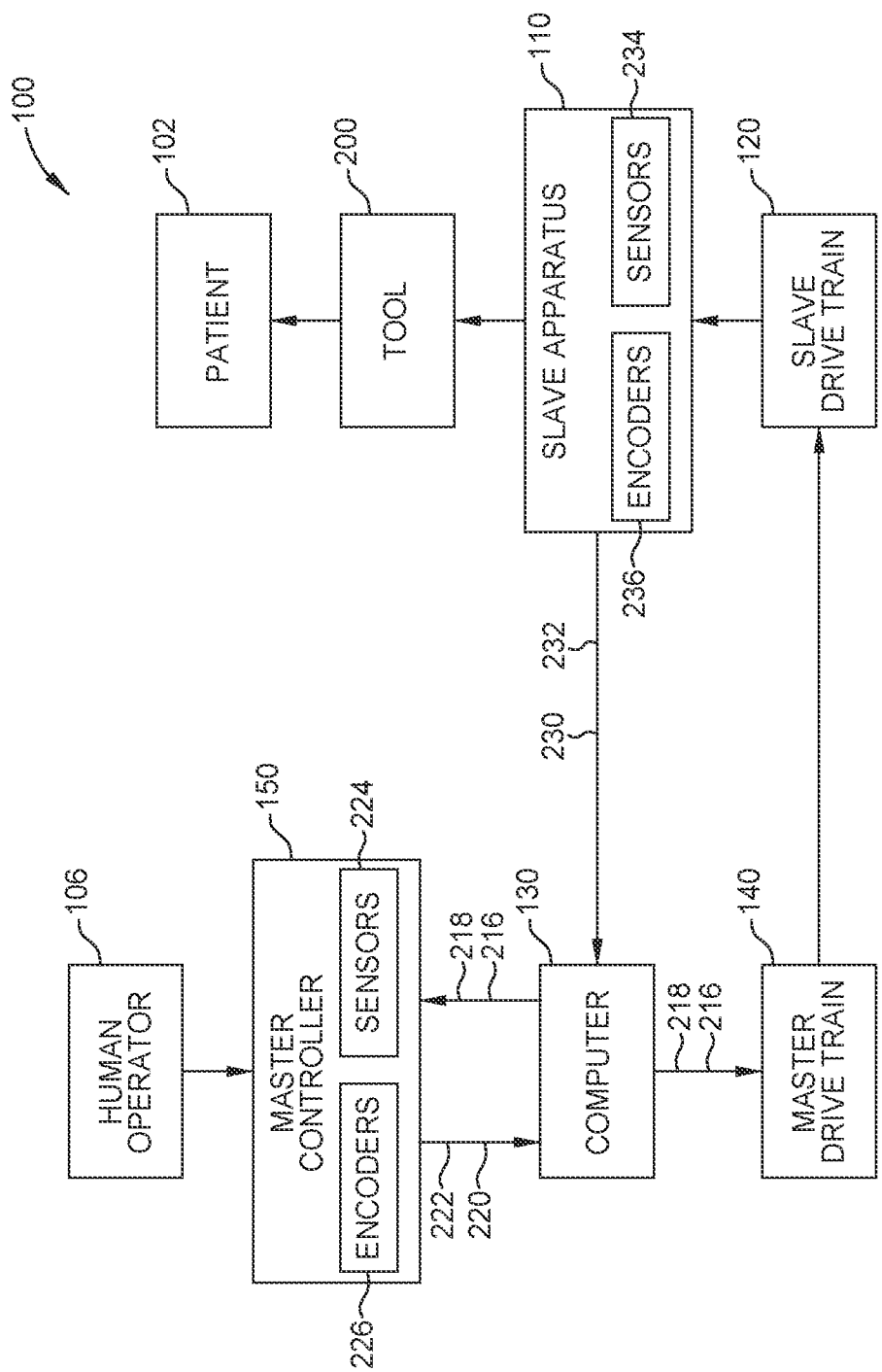
FIG. 2 illustrates a block diagram of the surgical manipulation system of FIG. 1, according to certain embodiments of the present disclosure.

FIG. 1 illustrates a schematic view of an exemplary surgical manipulation system 100 according to one embodiment described herein. FIG. 2 illustrates a block diagram of a signal flow of the surgical manipulation system of FIG. 1. Thus, FIG. 1 and FIG. 2 will be herein described together. Referring to FIG. 1 and FIG. 2, the surgical manipulation system 100 employs a master-slave type system that includes a slave apparatus 110 and a master controller 150. The master controller 150 may be any suitable type of six degrees of freedom (6-DOF) or seven degrees of freedom (7-DOF) master device with an operator interface. In one embodiment, the master controller 150 includes a 6-DOF or 7-DOF haptic interface. One such example of a suitable haptic interface is the Freedom6S haptic device available from MPB Technologies, Inc. In another embodiment, the master controller 150 includes a haptic interface modeled to match the slave apparatus 110. For example, the master controller 150 may have a structure substantially similar to that of the slave apparatus 110, as described below in greater detail. When an operator 106 operates the master controller 150, the master controller 150 generates a plurality of signals, herein collectively referred to as a "control signal," that is transmitted between a programmed computer 130, a master drive train 140, a slave drive train 120, and finally to the slave apparatus 110. Receiving the control signal, the slave apparatus 110 controls the operation of a surgical tool 200, described in further detail with reference to FIGS. 3A-3C.

Figure 3A:
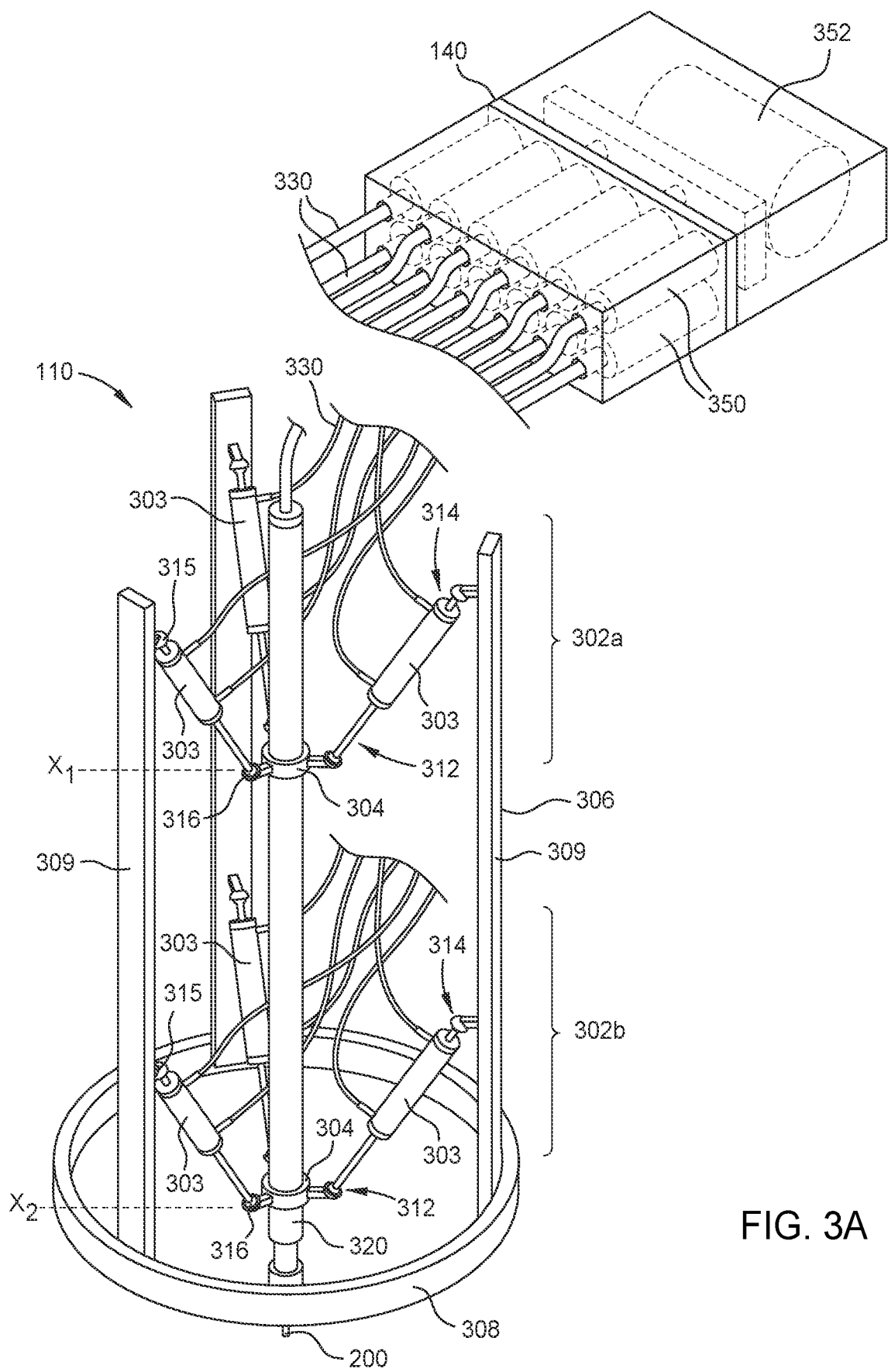
FIG. 3A illustrates an example perspective view of a slave apparatus of the surgical manipulation system of FIG. 1, according certain embodiments of the present disclosure.

When the surgical tool 200 is used, it may be directly or indirectly coupled to six actuator links 303 that act as the slave drive train 120 for the slave apparatus 110. For example, the surgical tool 200 may be indirectly coupled to six actuator links 303 via a tool shaft 320, as shown in FIG. 3A. The slave apparatus 110 controls the operation of the surgical tool 200 according to the control signal received from the master controller 150, and thus, performs surgical procedures on patient 102. The surgical tool 200 may be any suitable surgical device or apparatus for performance of ophthalmic surgical procedures, such as vitreoretinal surgical procedures. For example, the surgical tool 200 may be a saline hydraulic- or pneumatic-powered forceps, shaver, shear, cutter, or other non-actuated device. In some examples, the surgical tool 200 is configured to perform surgical maneuvers such as membrane peeling, segmentation, delamination of epiretinal membranes or the like. In some examples, the surgical tool 200 includes an end effector with additional actuators, such as rotary actuators, for enabling additional manipulation of a device or tool secured thereto. In other examples, the surgical tool 200 is a device holder or sleeve configured to secure another device or tool to the slave apparatus 110.

As an operator 106 manipulates the master controller 150, the movement drives six master motors of the master controller 150, causing six master encoders 226 of the master controller 150 to read different positions ($K_{P1}$) 222 of six master actuator links of the master controller 150. Simultaneously, six master force sensors 224 of the master controller 150 sense the movement of the master actuator links as they impart forces ($K_{F1}$) 220 on a structure of the master controller 150. In some embodiments, each master actuator link may correspond with at least one master encoder 226 and one master force sensor 224. Thus, although six master encoders 226 and six master force sensors 224 are described above, any suitable number may be utilized depending on the structure of the master controller 150.

The master force sensors 224 and the master encoders 226 act to send a plurality of values (e.g., signals) corresponding with the $K_{P1}$ 222 and $K_{F1}$ 220 to the computer 130, which then reads the values and applies various filtering 216 and scaling 218 (e.g., gain, reduction, compensation, adjustment) of the values, and sends an updated control signal to the master drive train 140 that drives the slave drive train 120 and the slave apparatus 110. The master drive train 140 includes drive motors 352 and master cylinders 350, described with more detail in reference to FIG. 3A. The signals instruct six drive motors 352 within the master drive train 140 to drive six hydraulic master cylinders 350 to move in a certain linear direction, causing linear actuation of the six actuator links 303 and/or rotational movement of a rotary actuator coupled directly or indirectly to the surgical tool 200 and/or the tool shaft 320. Thus, the slave apparatus 110 may be manipulated in a desired movement or to a desired position to perform surgical maneuvers with the surgical tool 200 on the patient 102. Similar as above, although six drive motors 352 and six hydraulic master cylinders 350 are described, any suitable number may be utilized depending on the structure of the master controller 150 and/or the slave apparatus 110.

The slave apparatus 110 optionally has a set of slave encoders 236 and slave force sensors 234. For example, the slave apparatus 110 includes a set of six slave encoders 236 and six slave force sensors 234, each slave encoder 236 and/or slave force sensor 234 corresponding with a single actuator link 303 and/or the surgical tool 200. In another example, the slave apparatus includes a set of seven or more slave encoders 236 and seven or more slave force sensors 234. In one embodiment, the master encoders 226 and/or the slave encoders 236 include fiber-optic-coupled sine-cosine (i.e., sine) encoders providing position and direction values of the master and/or the slave as analog sine waves. In one embodiment, the master encoders 226 and/or the slave encoders 236 include linear optical encoders, such as linear optical absolute encoders and linear optical incremental. In one embodiment, the master force sensors 224 and/or slave force sensors 234 include strain gauges. For example, the slave apparatus 110 may include disposable strain gauges 234 coupled to the surgical tool 200 and/or the actuator links 303 and configured to sense contact forces at the 30-320 Hz domain, otherwise known as the fidelity channel. In some embodiments, the slave apparatus 110 optionally includes a torque transducer or torque sensor configured to sense static and/or dynamic torque applied to the surgical tool 200. In some embodiments, the slave apparatus 110 includes a single force-sensing device configured to provide 6-DOF force feedback for the entire slave apparatus 110.

As the slave apparatus 110 is commanded to manipulate the surgical tool 200, the slave encoders 236 will read different positions ($K_{P2}$) 232 of the actuator links 303 and the slave force sensors 234 will simultaneously sense contact and torque forces ($K_{F2}$) 230 against the surgical tool 200. A plurality of corresponding values will then be sent back to the computer 130, which are filtered, scaled, and translated back to the master controller 150 and the operator 106. Generally, the $K_{P2}$ and $K_{F2}$ values 232, 230 are upscaled by the computer 130 for translation to the master controller 150 while the $K_{P1}$ and $K_{F1}$ values 222, 220 are downscaled for translation to the slave apparatus 110. In one embodiment, $K_P$ and $K_F$ values are scaled according to fixed scaling factors. In another embodiment, $K_P$ and $K_F$ values are scaled according to dynamic scaling factors.

The master motors for the master controller 150 are driven by the scaled signals and the operator 106 can sense contact with different types of surfaces and/or tissues during vitreoretinal surgery. In addition to translating signals between the master controller 150 and the slave apparatus 110, the computer 130 coordinates the actuator links of each of the master controller 150 and the slave apparatus 110. Kinematic and dynamic models are loaded into the computer 130 to stabilize the system and provide coordinated 6-DOF or 7-DOF motion to the slave apparatus 110 coupled to the surgical tool 200.

The execution of filtering 216 and scaling 218 of values by the computer 130 during transmission of values between the slave apparatus 110 and the master controller 150 provides numerous benefits during operation of the surgical manipulation system 100. Accordingly, many of the disadvantages that may be associated with manual surgery as well as conventional robotic surgical systems can also be averted. For example, involuntary operator movement or operator tremor (i.e., physiological tremor), which is very common with inexperienced or low volume surgeons as well as older surgeons, may be filtered by a tremor filter of the computer 130. Physiological tremor leads to an intolerable imprecision of surgical procedures that require a positioning accuracy of about 10 μm and below. Typically, physiological hand tremor lies in the band of 8-15 Hz with an amplitude of 50 μm and can be approximated by a sinusoidal movement, whereas controlled hand movement of a surgeon during microsurgeries (e.g., vitreoretinal surgery) is usually less than 1 Hz. For effective tremor filtering, the surgical manipulation system 100 may utilize one or more adaptive algorithms loaded into the computer 130 to create zero-phase lag in the filtering process to filter tremor from the master output in real-time. In one embodiment, filtering 216 is executed by a zero-phase delay low-pass filter (LPF) with a cut-off frequency of 5 Hz. For example, the filter may be a first-order Butterworth LPF.

As described above, the computer 130 is further configured to execute force downscaling, force limiting, position scaling, and velocity scaling between the master controller 150 and the surgical tool 200 during the scaling operations 218. Force downscaling, force limiting, and position and velocity scaling may be together described as the user interface control law embedded within the surgical manipulation system 100. As illustrated in FIG. 2, the surgical manipulation system 100 may utilize a closed control loop to control force and positioning of the slave apparatus 110. The closed control loop may further be utilized to provide haptic feedback to the operator 106 during use thereof. For example, the master force sensors 224 may sense operator forces upon the master controller 150, which may then be converted into downscaled control signals provided to the master drive train 140, slave drive train 120 and the slave apparatus 110. The sensed force values may be scaled by utilizing a software and user interface controllable scaling ratio or a fixed or predetermined scaling ratio loaded into the computer 130. In some examples, the computer 130 may be configured to execute cooperative control algorithms to generate movement of the slave apparatus 110 based on a scaled difference between tool-tissue and operator forces.

In addition to force control, the surgical manipulation system 100 provides a force or tactile (e.g., haptic) feedback signal between the surgical tool 200 and the master controller 150. In one embodiment, the surgical manipulation system 100 includes a haptic feedback system (e.g., feedback loop) separate from the closed control loop described above. In another embodiment, the haptic feedback loop is integrated with the force and positioning control loop. Generally, the haptic feedback loop collects and transmits tactile information between the surgical tool 200 and the master controller 150 in a domain of between about 30 Hz and up to about 320 Hz in order to enable the operator 106 to distinguish biomechanical properties of tissues during surgery.

FIG. 3A illustrates a perspective view of the slave apparatus 110 of the surgical manipulation system 100 according to one embodiment. As depicted in FIG. 3A, the slave apparatus 110 includes the tool shaft 320 movably coupled to two sets 302a, 302b of three radially-extending and linearly-actuating actuator links 303. The tool shaft 320 is configured to hold or mount the surgical tool 200 at a distal end thereof. The two sets 302a, 302b of actuator links 303 include a first proximal set 302a and a second distal set 302b having parallel kinematics, thus enabling the two sets 302a, 302b to linearly move in concert to manipulate the surgical tool 200 as desired. Utilization of a parallel and closed loop kinematic chain for the two sets 302a, 302b of actuator links 303 enables decreased structure weight and increased precision, stability, link rigidity, and acceleration as compared to an articulated arm equipped with serial kinematics. Additionally, unlike serial systems, joint error in the parallel structure of the slave apparatus 110 is averaged out. The parallel kinematic design of the slave apparatus 110 further enables differential drive of the two sets 302a, 302b of actuator links 303, thus providing greater maneuverability of the tool shaft 320 and surgical tool 200.

Each set 302a, 302b of actuator links 303 may be coupled to the tool shaft 320 at distal ends 312 of the actuator links 303 by a coupling ring 304 such that the actuator links 303 of each set 302a, 302b are attached to the tool shaft 320 on a single plane $X_1$ or $X_2$. The planes $X_1$ and $X_2$ are located at a proximal end 324 and a distal end 322 of the tool shaft 320, respectively. Accordingly, the embodiment depicted in FIG. 3A may be described as a dual tripod slave apparatus 110, as two sets 302a, 302b of three actuator links 303 (e.g., "three plus three") extend radially outward from the tool shaft 320 at two different horizontal planes $X_1$ and $X_2$, thus forming two tripods of actuator links 303. Thus, the actuator links 303 may be radially spaced apart from adjacent actuator links 303 of the same set 302 by an angle of about 120°. Although three actuator links 303 are depicted in each set 302a, 302b in FIG. 3A, it is contemplated that other quantities of actuator links 303 may be utilized in each set 302a, 302b. In some examples, a single set 302a, 302b may comprise four or more actuator links 303. Wherein in more than three actuator links 303 are included in each set 302a, 302b, a radial spacing between each actuator link 303 may be less than 120°. Furthermore, although the actuator links 303 are depicted as coupled to the coupling rings 304, the actuator links 303 may be directly coupled to the tool shaft 320 or the surgical tool 200 via spherical joints in some embodiments.

Each actuator link 303 is further coupled to a support frame 306 at a proximal end 314 of the actuator link 303 disposed at a location above the distal end 312 thereof and radially outward of the surgical tool 200. Accordingly, the actuator links 303 may be described as being vertically angled (e.g., non-parallel to a horizontal axis X or horizontal axis Z of the slave apparatus 110). The support frame 306 may include any suitable structure as necessary to support the quantity of actuator links 303 utilized for the slave apparatus 110. As depicted in FIG. 3A, the support frame 306 includes a ring-like base 308 and three support columns 309 extending upwardly therefrom, which may be parallel to a vertical axis Y of the slave apparatus 110. The three-support columns 309 act as anchoring points for the actuator links 303, which may be coupled to the support columns 309 by any suitable type of spherical joints 315 enabling 3-DOF rotational movement. For example, the spherical joints 315 may have a ball-and-socket design, similar to that of the human hip joint, allowing free rotation of the actuator links 303 in two planes, while also preventing translation in any direction.

Likewise, the distal ends 312 of the actuator links 303 may also be coupled to the coupling ring 304, tool shaft 320, or surgical tool 200 by a spherical joint 316. Accordingly, the utilization of two spherical joints 315, 316 at opposing ends of the actuator links 303 enables movement of the surgical tool 200 in all three planes. Thus, the actuator links 303 may provide x, y, and z transitional movement as well as pitch and yaw rotational movement for the surgical tool 200, enabling up to 6-DOF of mobility for the surgical tool 200.

In some embodiments, the slave apparatus 110 further includes a rotary actuator to provide 360° rotational movement of the tool shaft 320 and/or the surgical tool 200, thus enabling redundant 7-DOF tool roll of the surgical tool 200. In some embodiments, the tool roll axis is redundant and only does tool roll (and not pitch or yaw). In this embodiment, tool pitch and yaw may be accomplished along with tool translation by the dual tripod structure and it's six actuators. In one embodiment, the rotary actuator is coupled to or disposed within one of the one or more coupling rings 304 or the tool shaft 320, and thus may directly rotate the surgical tool 200. In another embodiment, the rotary actuator is coupled to the ring-like base 308, enabling rotation of the support columns 309 and ultimately, the surgical tool 200. The rotary actuator may include any suitable type of rotary mechanism, including a zero-backlash piston driven rack and pinion, a single or dual rotary vane saline hydraulic actuator, and the like. In some embodiments, the slave apparatus 110 also optionally includes a torque transducer or torque sensor coupled to or disposed within the one or more coupling rings 304 or the tool shaft 320 the coupling rings 302 for torque feedback.

The slave apparatus 110 is generally configured to be coupled to the head of a patient and specifically, over the pars plana of the patient's eye to perform vitreoretinal surgery. Accordingly, the components of the slave apparatus 110 are generally formed of lightweight and disposable materials such as fiber reinforced engineering plastics, aluminum, Kevlar, carbon fiber, or the like. Furthermore, the actuator links 303 and rotary actuators utilize a hydraulic drive system to manipulate the surgical tool 200. Utilization of hydraulic actuator links 303 with intrinsic, very low friction saline hydrostatic bearings enables high power density while maintaining a low mass and low volume architecture of the slave apparatus 110, partly due to the greatly reduced friction provided by hydrostatic bearings. Additionally, a hydraulic drive system avoids exposure of the patient to electromagnetic interference (EMI) or radio-frequency interference (RFI) as is associated with electric motors, and further prevents spring-related control issues associated with pneumatic drive systems. In one embodiment, the actuator links 303 include linear near-zero friction hydraulic piston-cylinder sets to enable linear extension and retraction the actuator links 303, and thus, manipulation of the surgical tool 200. The fluid maintained within the hydraulic system can be pressurized sterile water, sterile saline, or other suitable sterile and biocompatible fluids. The lightweight architecture and hydraulic drive system of the slave apparatus 110 enables the slave apparatus 110 to be mounted on a patient's head without causing any discomfort to the patient. By mounting the slave apparatus 110 to the patient's head, the risks associated with uncontrolled patient movement of the head and/or eye during surgery can be eliminated.

The actuator links 303 of the slave apparatus 110 are indirectly coupled to the master drive train 140 via a plurality of stiff hydraulic fluid lines (HFLs) 330 to avoid phase delay. The HFLs 330 are formed of any material having a suitable stiffness and pressure rating. In one embodiment, the HFLs 330 are formed of polyvinyl chloride (PVC), polyethylene (PE), high-density polyethylene (HDPE), cross-linked polyethylene (XLPE), or the like. During surgery, the remote master drive train 140 is placed in the vicinity of the patient so as to decrease momentum of fluid moving within the HFLs 330 as well as to decrease fluidic resistance therethrough. Generally, the master drive train 140 is an electrohydraulic system and includes six master cylinders 350 coupled to six slotless, brushless DC (BLDC) drive motors 352. The utilization of slotless BLDC-type linear motors provides several advantages over other types of motors (e.g., slotted motors) such as extremely small cogging torque (e.g., torque ripple). Thus, slotless BLDC-type motors enable more accurate driving with reduced vibration and noise during use thereof. In one embodiment, the drive motors 352 utilize a neodymium iron boron (NdFeB) magnet as a permanent magnet. Together with the actuator links 303 of the slave apparatus 110 and the master cylinders 350, the drive motors 352 form a direct drive system that enables the surgical manipulation system 100 to better perform force control, as geared drive systems may suffer from the effects of friction and backlash.

Figure 3B:
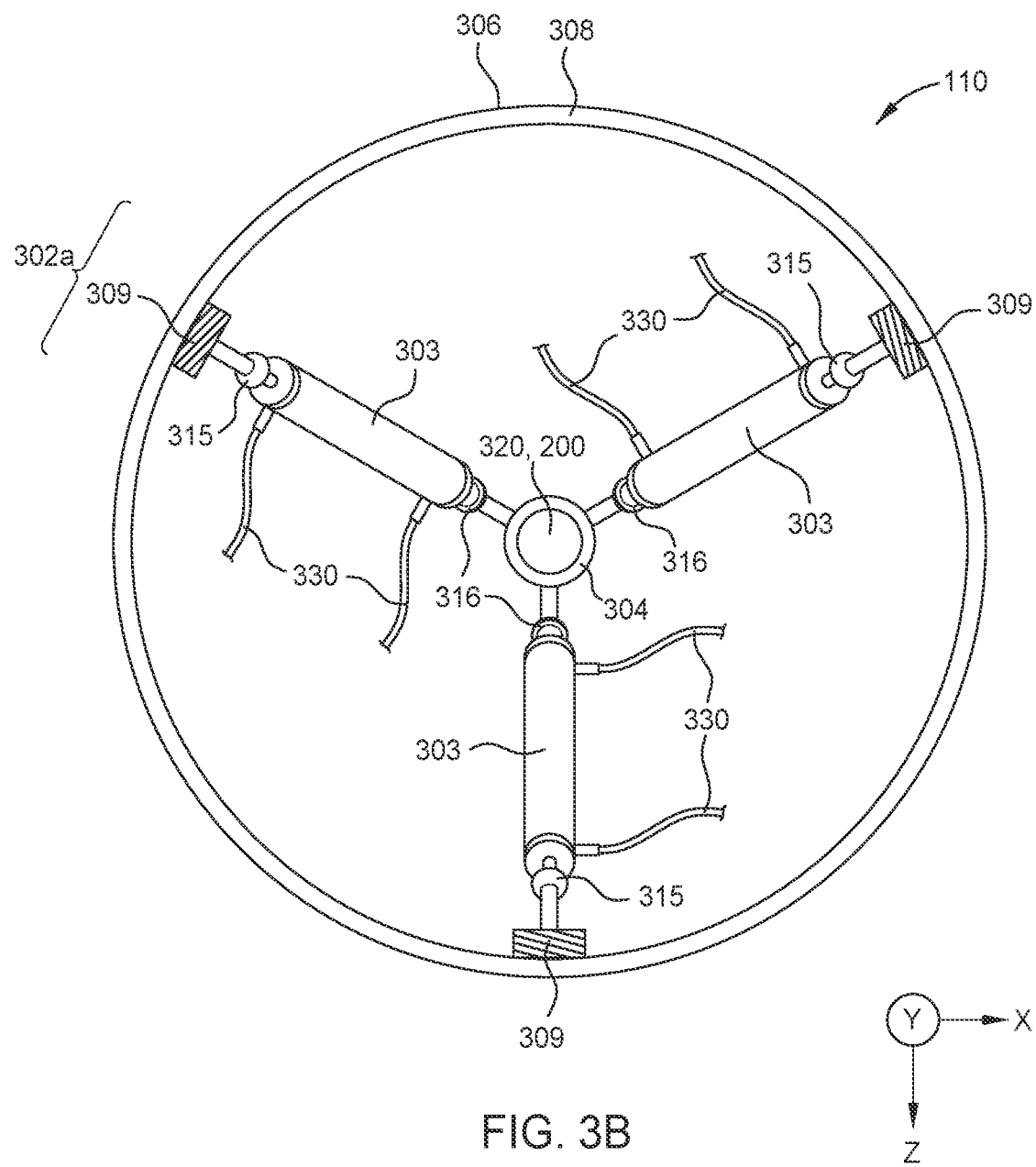
FIG. 3B illustrates an example schematic top-down view of the slave apparatus of FIG. 3A, according to certain embodiments of the present disclosure.

FIG. 3B illustrates a schematic top-down view of the dual tripod slave apparatus 110 previously described with reference to FIG. 3A. The slave apparatus 110 in FIG. 3B has two sets 302a, 302b of three actuator links 303, wherein each actuator link 303 is radially spaced from an adjacent actuator link 303 of the same set by an angle of about 120°. Further, each actuator link 303 is horizontally or radially aligned (e.g., disposed directly above or below on the axis Y when in a neutral position) with an actuator link 303 of an adjacent set 302 above or below in relation thereto. Thus, only one set 302a of actuator links 303 is visible in the foreground of FIG. 3B, and only three support columns 309 are necessitated for anchoring the actuator links 303 to the support frame 306. Accordingly, the structure of the actuator links 303 depicted in FIGS. 3A and 3B may be described as "horizontally aligned".

Figure 3C:
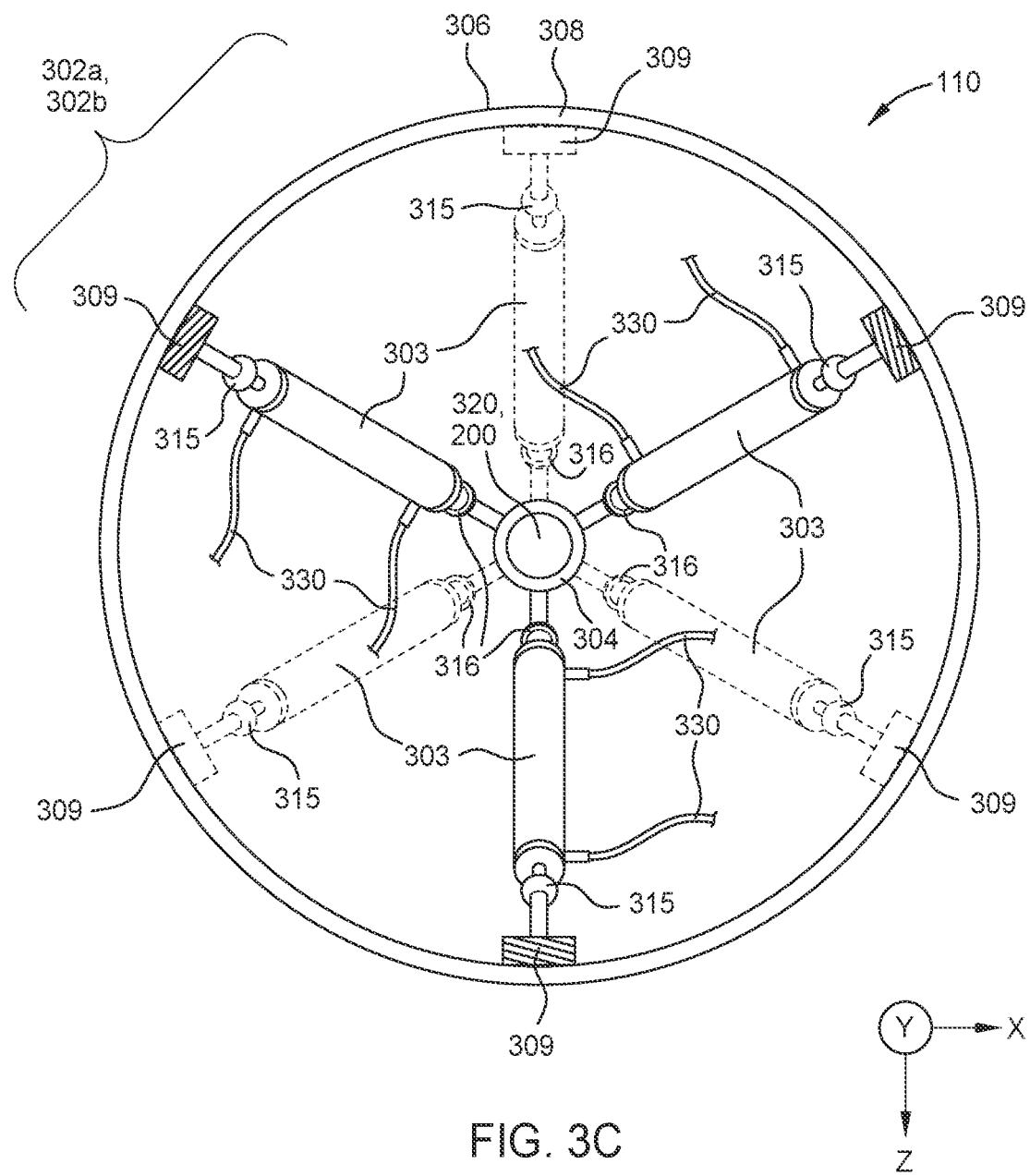
FIG. 3C illustrates an example schematic top-down view of the slave apparatus of FIG. 3A, according to certain embodiments of the present disclosure.

FIG. 3C illustrates a schematic top-down view of the dual tripod slave apparatus 110 wherein the actuator links 303 are horizontally or radially offset (e.g., unaligned on the axis Y). As depicted in FIG. 3C, the slave apparatus 110 still maintains a dual tripod structure having two sets 302a, 302b of three actuator links 303 radially spaced apart at an angle of about 120°. However, unlike the embodiments discussed with reference to FIGS. 3A and 3B, each actuator link 303 is horizontally unaligned with the actuator link 303 of the adjacent set 302 disposed above or below in relation thereto. Thus, both sets 302a, 302b of actuator links 303 are visible in FIG. 3C (one set 302b is shown in phantom), and three additional support columns 309 are utilized to support one set 302 of actuator links 303. The utilization of this horizontally or radially offset structure of the actuator links 303 may enable a different degree of mobility (e.g., range of articulation) for the surgical tool 200 compared to the horizontally aligned structure described above, and thus, may be preferred in some instances.

Figure 4:
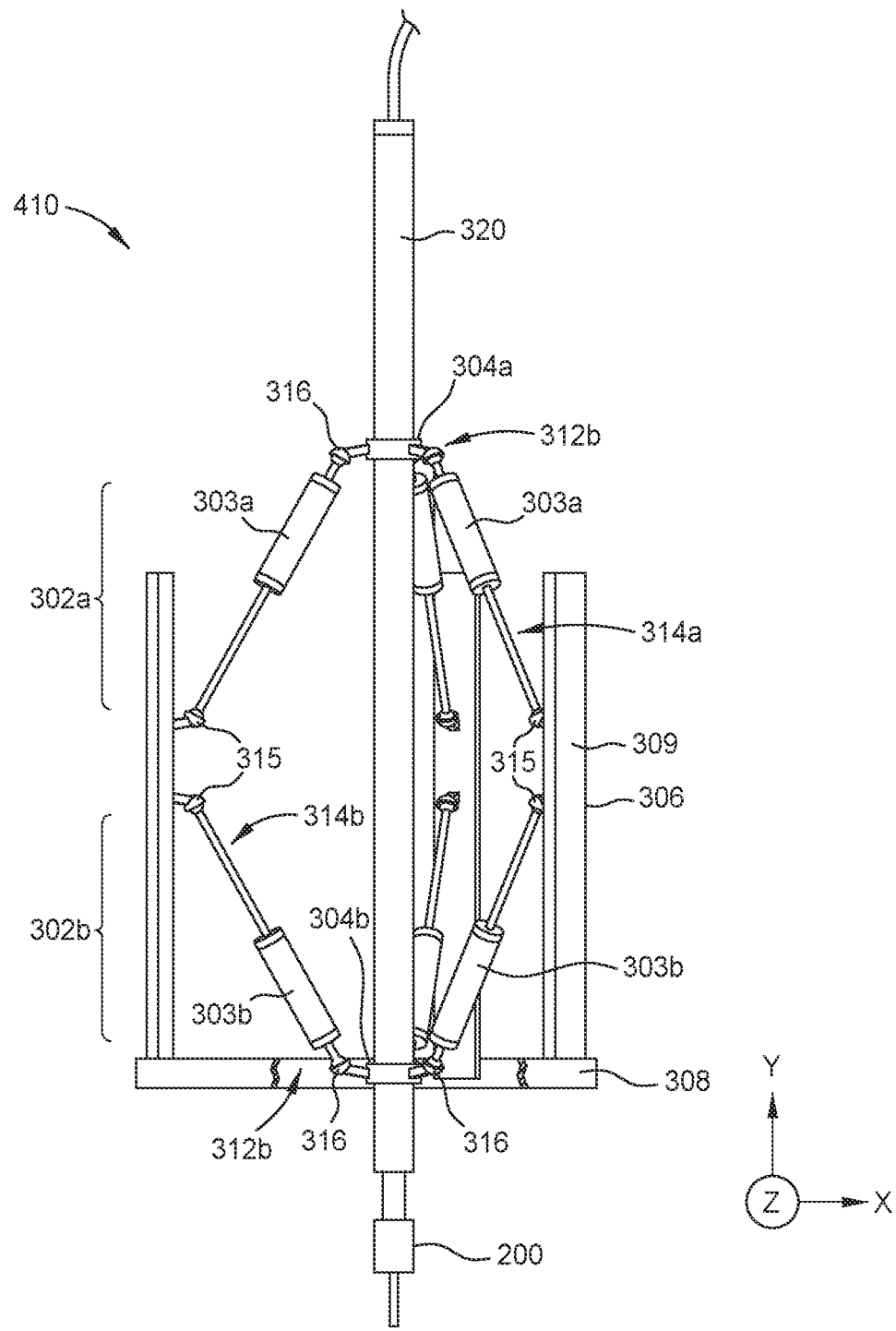
FIG. 4 illustrates a perspective view of another example slave apparatus configured to be utilized with the surgical manipulation system of FIG. 1, according to certain embodiments of the present disclosure.

FIG. 4 illustrates a perspective view of an alternative slave apparatus 410 of the surgical manipulation system 100 according to one embodiment. As depicted in FIG. 4, the relationships of the vertical positions of the distal ends 312 and the proximal ends 314 of the actuator links 303 (e.g., the vertical orientations or angles of the actuator links 303) between each set 302a, 302b are inverted. That is, in one set 302a, the distal ends 312a of the actuator links 303a are coupled to the tool shaft 320 or surgical tool 200 at the coupling ring 304a, which is disposed at a position along a length of the surgical tool 200 located above the coupling point of the proximal ends to the support columns 309. Conversely, the distal ends 312b of the actuator links 303b are coupled to the tool shaft 320 or surgical tool 200 at the coupling ring 304b disposed at a position located below the coupling point of the proximal ends 314b to the support columns 309. This alternative embodiment differs from those described with reference to FIGS. 3A-3C, wherein the both sets of actuator links 302a, 302b have substantially similar vertical orientations and/or angles.

Figure 5:
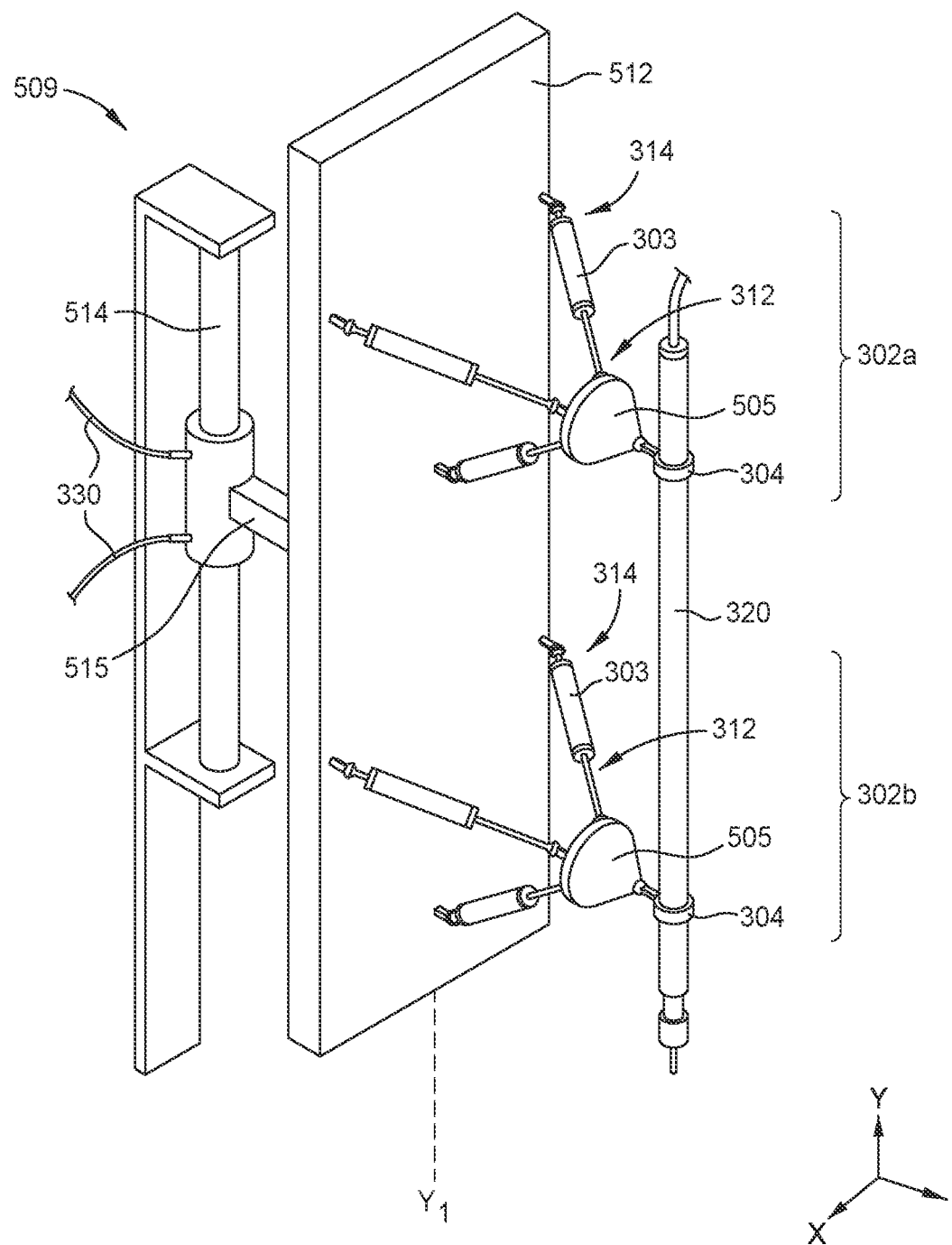
FIG. 5 illustrates a perspective view of another example slave apparatus configured to be utilized with the surgical manipulation system of FIG. 1, according to certain embodiments of the present disclosure.

FIG. 5 illustrates a perspective view of an alternative slave apparatus 510 of the surgical manipulation system 100 according to one embodiment. Similar to the slave apparatus 110 and 410, the slave apparatus 510 includes two sets 302a, 302b of three actuator links 303, each indirectly coupled to the tool shaft 320 or the surgical tool 200 at the distal ends 312 and at different points along the length of the surgical tool 200. However, unlike the embodiments described above, the two sets 302a, 302b of actuator links 303 are directly or indirectly coupled to a single actuation column 509 at the proximal ends 314 such that the proximal ends 314 are aligned along a single vertical plane Yi. The single actuation column 509 acts in a similar manner to the support columns 309 and may couple to the base 308 at a lower end thereof. Furthermore, the distal ends 312 of the actuator links 303 in each set 302a, 302b are coupled to the coupling rings 304 via an intermediary platform 505, upon which the distal ends 312 of the actuator links 303 in each set 302a, 302b converge to couple thereto.

As depicted in FIG. 5, the proximal ends 314 of the actuator links 303 are indirectly coupled to the actuation column 509 via an actuating platform 512. The actuating platform 512 movably couples to the actuation column 509 at a rotational hinge 514 via a lever arm 515 and provides a movable extension thereof. In some embodiments, the rotational hinge 514 utilizes rotational or linear hydraulics to actuate the actuating platform 512 in a horizontal (e.g., along the axis Z or X) and/or vertical direction (e.g., along the axis Y). In further embodiments, the actuating platform 512 is coupled to the lever arm 515 via another rotational joint with rotational hydraulics, thus enabling further horizontal rotational movement of the actuating platform 512. Similar to the support frame 306, the actuation column 509 may be coupled to the base 308, which may have any suitable morphology such as a ring-like shape.

The intermediary platforms 505 at the distal ends 312 of the actuator links 303 enable translation of linear movement from actuator links 303 to corresponding transitional and rotational manipulation of the surgical tool 200. Accordingly, both sets 302a, 302b of actuator links 303 may act in concert to provide x, y, and z transitional movement as well as pitch and yaw rotational movement. In combination with the utilization of a rotary actuator that may be coupled to the coupling rings 304 and/or tool shaft 320, the actuator links 303 enable up to 7-DOF of the surgical tool 200. Although depicted having a conical shape, the intermediary platforms 505 may have any suitable morphology to enable translation of the linear movement of the actuator links 303 to 6-DOF movement of the surgical tool 200.

Although the structures depicted in FIGS. 3A-3C, 4, and 5 are described with reference to the slave apparatus 110, the same or substantially the same structures may be utilized for the master controller 150 in combination with the slave apparatuses 110, 410, and 510 described above. For example, when utilizing the dual tripod slave apparatus 110, the master controller 150 may mimic the slave apparatus 110 and share the same dual tripod structure, but scaled up for easier manipulation by the operator 106. Thus, the master controller 150 may include a replica surgical tool handle coupled to two sets of three radially extending master actuator links, substantially similar in structure to the sets 302a, 302b of actuator links 303 utilized for the slave apparatus 110, wherein each set of master actuator links is coupled to the replica surgical tool handle along a single horizontal plane to form a dual tripod structure. Each actuator link 303 and/or the replica tool handle may include one or more master encoders 226 and one or more master force sensors 224 communicatively coupled thereto and configured to provide 6-DOF force and tactile feedback. For example, the master encoders 226 may include a rotary encoder communicatively coupled to the replica tool handle to sense static and/or dynamic torque applied thereto. Further, the master controller 150 may optionally include slotless BLDC-type master motors, which in combination with the rotary encoders, enable torque feedback. The master controller 150 may further include a master supporting frame having a base and three or more support columns extending therefrom and coupled to proximal ends of the master actuator links.

By mimicking the mechanical structure of the slave apparatus 110 for the master controller 150, complete general spatial motion of the slave apparatus 110 and thus, the surgical tool 200, is enabled. Furthermore, mimicking of the mechanical structure of the slave apparatus 110 for the master controller 150 may improve ease of use for the operator 106, as the positions for the slave apparatus 110 and the master controller 150 may be made identical but for structure scaling. The dual tripod structure of the master controller 150 also enables the operator 106 to perform surgical procedures with the surgical manipulation system 100 utilizing only one hand, and thus, the operator 106 may simultaneously use his or her other hand for other actions such as for positioning of an endoilluminator. In some embodiments, a pair or surgical manipulation systems 100 may be utilized in combination to perform two-handed surgery by the operator 106, each hand of the operator 106 controlling an individual surgical manipulation system 100 and thus, an individual slave apparatus 110.

Figure 6A:
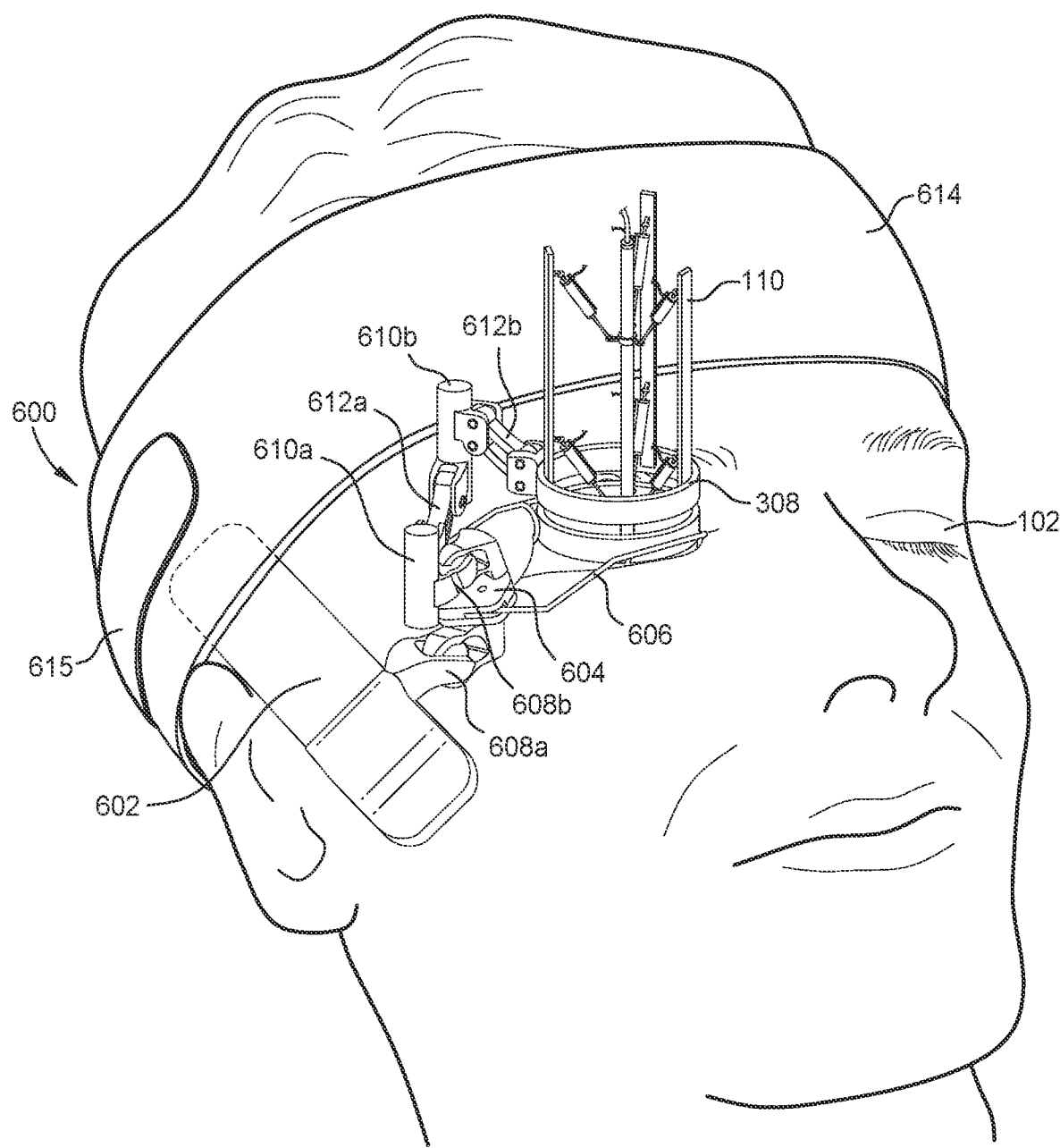
FIG. 6A illustrates a perspective view of an example slave apparatus mounted to a patient's head, according to certain embodiments of the present disclosure.
Figure 6B:
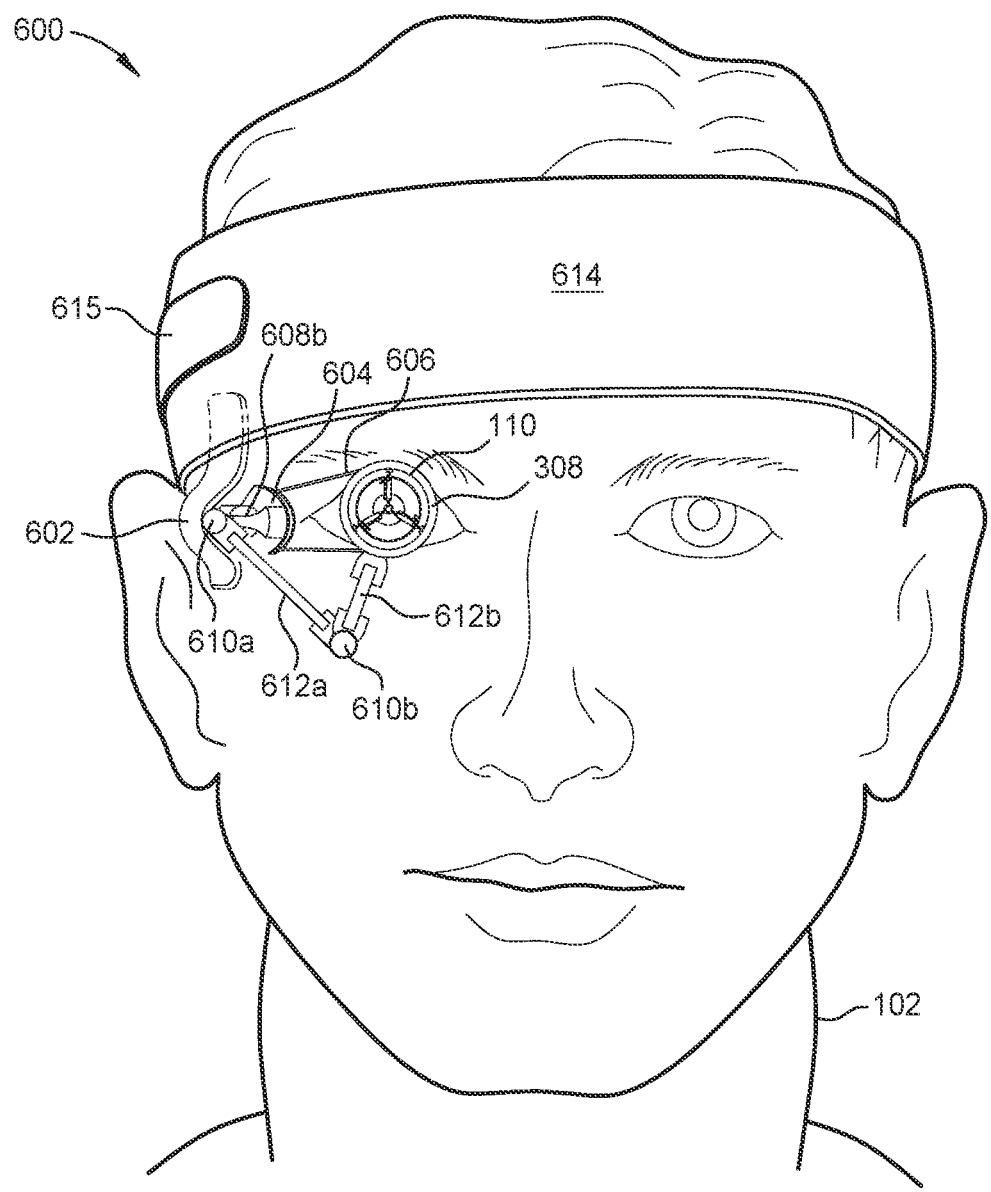
FIG. 6B illustrates a perspective view of an example slave apparatus mounted to a patient's head, according to certain embodiments of the present disclosure.

FIGS. 6A and 6B illustrate perspective views of the slave apparatus 110 when mounted to the head of the patient 102, according to some embodiments. Accordingly, FIGS. 6A and 6B are herein described together for clarity. The slave apparatus 110 depicted in FIGS. 6A and 6B is coupled to a slave apparatus support system 600 including a temple support pad 602, a main body 604, a speculum 606, a plurality of spherical joints 608a, 608b, a plurality of rotational joints 610a, 610b, a plurality of articulated linkages 612a, 612b, and a headband 614. The slave apparatus support system 600 aids in supporting the slave apparatus 110 in an upright and secured (e.g., fixed) position by providing a three point fixation while the slave apparatus 110 is coupled to the patient's head. Thus, when attached to the slave apparatus support system 600 and mounted on the patient's head, the slave apparatus 110 will move with the patient's head, thereby eliminating the need for providing general anesthesia and/or a neuromuscular blockade to the patient to prevent patient movement that may disrupt utilization of the surgical tool 200 or lead to surgical instrument-caused damage of the patient's eye. Accordingly, the risks associated with involuntary movement of the patient may be eliminated by utilizing the slave apparatus 110 along with the slave apparatus support system 600.

As depicted in FIGS. 6A and 6B, the temple support pad 602 is coupled to the main body 604 via a first spherical joint 608a. The first spherical joint 608a enables adjustment of the temple support pad 602 to provide flexible positioning of the temple support pad 602 with respect to the patient 102, thus enabling optimal support for the slave apparatus 110. Upon adjustment of the temple support pad 602 to a desired position, the first spherical joint 608a may be locked in place using any suitable locking mechanism, such as a friction-type locking mechanism (e.g., a threaded mechanism). In addition to the main body 604, the temple support pad 602 also couples to the headband 614 for further stabilization of the slave apparatus support system 600. The headband 614 is configured to wrap around the head of the patient and is adjustable in size to enable a customized fit with respect to the patient. Generally, the headband 614 is adjustable via any suitable fastening mechanism. In one example, the headband 614 may be adjustable via a hook and loop fastener 615, for example, Velcro®.

The main body 604 may rest on the patient when the slave apparatus support system 600 is used during vitreoretinal surgery. Coupled to the main body 604 is the speculum 606 having any suitable kind of speculum blades (e.g., wire speculum blades). The speculum 606 is used to hold open the eyelids of the patient during vitreoretinal surgery, and may further provide mechanical support and stability to the slave apparatus support system 600 by contributing to the stabilization of the main body 604. Also coupled to the main body 604 is a second spherical joint 608b, which may be substantially similar to the first spherical joint 608a described above. The second spherical joint 608b may provide a means to orient one or more axes of movement of the slave apparatus 110 by virtue of attachment via the articulated linkages 612. Similar to the first spherical joint 608a described above, the second spherical joint 608b may be locked in place using any suitable locking mechanism, such as a friction-type locking mechanism.

Also depicted in FIGS. 6A and 6B are the rotational joints 610a, 610b. The rotational joints 610a, 610b are coupled to two articulated linkages 612a, 612b and enable the articulated linkages 612a, 612b to rotate laterally about a pivot point through each rotational joint 610a, 610b. In one embodiment, the rotational joints 610a, 610b are cylindrical free-rotating parallel joints, and thus, may enable lateral positioning of the slave apparatus 110 in combination with the articulated linkages 612a, 612b. In some embodiments, at least one of the rotational joints 610a, 610b may be restricted to a certain degree of rotation, such as to a limited angular range. The articulated linkages 612a, 612b may be any suitable kind of linkages that enable vertical adaptation of the slave apparatus 110 relative to the speculum blades of the speculum 606, thus further enabling accommodation of the patient's anatomical characteristics. As shown in FIGS. 6A and 6B, the slave apparatus 110, and in particular, the base 308, is coupled to the articulated linkage 612b.

FIG. 6C illustrates a cross-sectional view of a portion of the slave apparatus 110 while coupled to the eye 670 of the patient 102, according to an embodiment. As depicted, the slave apparatus 110 includes a hub 630 with one or more retention elements 632 coupled to a distal end 650 of the slave apparatus 110. As shown, the slave apparatus 110 is placed on the eye 670 such that the bottom surface 634 of hub 630 is contacted against the surface of eye 670 (i.e., the surface of the outermost layer of the eye, referred to as the sclera). The hub 630 may have any suitable morphology for coupling the slave apparatus 110 to the eye, including a ring-shape or cylindrical shape, among other morphologies. Although depicted as a separate component in FIG. 6C, the hub 630 may be integrated with the base 308 such that the base 308 and the hub 630 are a single, integral component in some embodiments.

As shown, the retention elements 632 are coupled to bottom surface 634 of hub 630. In the example of FIG. 6C, the retention elements 632 are curved needles (e.g., hooks) that extend from the bottom surface 634 down into the eye 670. In certain embodiments, the retention elements 632 may extend between about 200 and about 600 microns into the eye 670. When the retention elements 632 are placed on the surface of the eye 670, rotating the hub 630 towards a direction in which the tips of the retention elements 632 are directed to, causes the retention elements 632 to penetrate into the one or more outermost layers of eye 670, such as the sclera. For example, the operator 106, such as a surgeon, may rotate the hub 630 in a clock-wise manner (e.g., using fingers or a surgical instrument, such as forceps), causing the tips of the retention elements 632 to penetrate the eye 670. By continuing to rotate the hub 630, the retention elements penetrate deeper into the eye 670 until the bottom surface 634 is disposed against the outer surface of the eye 670. Once the bottom surface 634 of the hub 630 touches the outer surface of eye 670, the slave apparatus 110 may be completely secured against the eye 670.

By directly coupling the slave apparatus 110 to the eye 670, the surgical manipulation system 100 may be utilized without an eye tracking system as the hub 630 stabilizes and secures slave apparatus 110 in place. Furthermore, direct coupling of the slave apparatus 110 to the eye 670 limits any residual motion caused by incomplete blockade of extraocular eye muscles by retrobulbar anesthetic blocks, which are typically utilized to provide akinesia and anesthesia during ophthalmic procedures. Thus, utilization of the slave apparatus 110 in combination with the hub 630 would eliminate or reduce any harmful effects caused by involuntary movement of the patient's eye during surgical procedures.

In summary, embodiments of the present disclosure include devices and systems for improving the accuracy and dexterity of ophthalmic surgical interventions while minimizing trauma to the patient. The devices and systems described herein include embodiments wherein a surgeon may mount and secure a surgical slave apparatus to the head of a patient such that the slave apparatus moves along with the head of a patient during use thereof. Furthermore, the devices and systems described herein include embodiments wherein the slave apparatus may be secured directly to the eye of a patient, thus stabilizing the eye in locked position and preventing any involuntary movement thereof. Accordingly, the described embodiments eliminate the need for the provision of general anesthetics with neuromuscular blockade, which are utilized in part to prevent patient movement. Voluntary and involuntary patient movement during surgical procedures, and in particular, delicate and precise procedures such as vitreoretinal surgery, may cause undesired and accidental contact between surgical tools and ocular tissues. Such contact may lead to serious complications to the patient's eye, which can develop into potentially irreversible damage and visual impairment. By utilizing the devices and systems described herein, many of the risks associated with patient movement during ophthalmic surgical procedures may be reduced or eliminated.

Still further, the devices and systems described herein may mitigate some of the inherent restrictions on vitreoretinal surgery related to human sensory and motor limitations. For example, surgeon fatigue, hand tremor, and the inability to perceive miniscule tactile differences between tissues in the ocular space are common limitations on the accuracy and effectiveness of vitreoretinal procedures. By providing mechanisms for force control (e.g., scaling and filtering) and feedback (e.g., tactile feedback) while maintaining 7-DOF movement, the devices and systems described herein provide surgeons with increased dexterity and precision wherein the surgeon has an improved physical connection with the surgical site. Thus, the devices and systems described herein may decrease the risk of surgical error and reduce operative times, thereby increasing the overall effectiveness of vitreoretinal procedures.

Although vitreous surgery is discussed as an example of a surgical procedure that may benefit from the described embodiments, the advantages of the surgical devices and systems described herein may benefit other surgical procedures as well.

While the foregoing is directed to embodiments of the present disclosure, other and further embodiments of the disclosure may be devised without departing from the basic scope thereof, and the scope thereof is determined by the claims that follow.

What is claimed is:

1. A surgical system for manipulating a surgical tool, comprising:
    a master apparatus; and
    a slave apparatus controllably coupled to the master apparatus and configured to be mounted to a patient's head, the slave apparatus comprising:
        a support frame comprising a base and one or more support columns extending therefrom in a first orientation;
        a first set of three hydraulically-driven and linear-actuating links, each link of the first set coupled to a respective one of the one or more support columns at a proximal end of the link by a spherical joint, each link of the first set further configured to directly or indirectly couple to the surgical tool at a distal end of the surgical tool and provide translational and rotational movement to the surgical tool, wherein each link of the first set is radially spaced apart from an adjacent link in the first set by an angle less than or equal to about 120 degrees;
        a second set of three hydraulically-driven and linear-actuating links, each link of the second set coupled to a respective one of the one or more support columns at a proximal end of the link by a spherical joint, each link of the second set further configured to directly or indirectly couple to the surgical tool at a proximal end of the surgical tool and provide translational and rotational movement to the surgical tool, wherein each link of the second set is radially spaced apart from an adjacent link in the second set by an angle less than or equal to about 120 degrees; and
        a hydraulically-driven rotary actuator, the rotary actuator configured to provide a rotational movement to the surgical tool coupled to the first and second sets of links.

2. The surgical system of claim 1, wherein the slave apparatus is further coupled to a slave apparatus support system comprising:
    an adjustable temple support pad; a speculum; and
    an adjustable headband, wherein the slave apparatus support system provides at least a three-point fixation when mounted to a patient's head to stabilize the slave apparatus in an upright and secured position.

3. The surgical system of claim 2, wherein the slave apparatus further comprises:
a hub coupled to a distal end of the slave apparatus, the hub comprising one or more retention elements on a bottom surface thereof, the retention elements configured to penetrate into one or more outermost layers of a patient's eye to secure the slave apparatus against the eye.

4. The surgical system of claim 1, wherein distal ends of the links within the first set are coupled to a coupling ring along a first plane, and wherein each set of the links extend radially outward from the coupling ring.

5. The surgical system of claim 4, wherein each link is aligned with another link of the second set along the first plane when the surgical system is in a neutral position.

6. The surgical system of claim 4, wherein each link of the first set is offset with the links of the second set along the first plane when the surgical system is in a neutral position.

7. The surgical system of claim 1, wherein the surgical tool is a tool shaft configured to mount another surgical device.

8. The surgical system of claim 1, wherein the slave apparatus provides up to 7-DOF movement to the surgical tool.

9. The surgical system of claim 1, further comprising:
a master drive train coupled to the first and second sets of links via a plurality of hydraulic fluid lines, the master drive train comprising:
six slotless, brushless, linear DC motors; and
six linearly-actuating master cylinders.

10. The surgical system of claim 9, wherein a fluid maintained in the linearly-actuating master cylinders, hydraulic fluid lines, and first and second sets of links comprises sterile water, saline, or perfloro-octane.

11. The surgical system of claim 1, wherein the slave apparatus and the master apparatus comprise six force sensors.

12. The surgical system of claim 11, wherein the slave apparatus and master apparatus form a closed control loop for force signal values detected by the force sensors and translated between the slave apparatus and master apparatus.

13. The surgical system of claim 12, further configured to limit and scale the force signal values translated between the master apparatus and the slave apparatus.

14. The surgical system of claim 1, wherein the slave apparatus or master apparatus comprise six sine-cosine encoders.

15. The surgical system of claim 14, further configured to scale position signal values collected by the encoders and translated between the master apparatus and the slave apparatus.

16. A surgical system for manipulating a surgical tool, comprising:
a master apparatus; and
a slave apparatus controllably coupled to the master apparatus and configured to be mounted to a patient's head, the slave apparatus comprising:
an actuating platform;
a first set of three hydraulically-driven and linear-actuating links, each link of the first set coupled to the actuating platform at a proximal end of the link by a spherical joint, each link of the first set further configured to directly or indirectly couple to the surgical tool at a distal end of the surgical tool and provide translational and rotational movement to the surgical tool;
a second set of three hydraulically-driven and linear-actuating links, each link of the second set coupled to the actuating platform at a proximal end of the link by a spherical joint, each link of the second set further configured to directly or indirectly couple to the surgical tool at a proximal end of the surgical tool and provide translational and rotational movement to the surgical tool; and
a hydraulically-driven rotary actuator, the rotary actuator configured to provide a rotational movement to the surgical tool coupled to the first and second sets of links.

17. The surgical system of claim 16, wherein the actuating platform is further coupled to a support column via a lever arm and rotation hinge, the actuating platform configured to be translationally actuated in at least a first and second direction.

18. The surgical system of claim 16, wherein the distal ends of the first and second sets of the links converge upon and couple to an intermediary platform disposed between each of the first and second sets and a coupling ring.

\* \* \* \* \*